US006689323B2

(12) United States Patent
Fisher et al.

(10) Patent No.: US 6,689,323 B2
(45) Date of Patent: Feb. 10, 2004

(54) METHOD AND APPARATUS FOR LIQUID TRANSFER

(75) Inventors: William D. Fisher, San Jose, CA (US); Richard P. Tella, Sunnyvale, CA (US); Michael P. Caren, Palo Alto, CA (US)

(73) Assignee: Agilent Technologies, Palo Alto, CA (US)

( * ) Notice: Subject to any disclaimer, the term of this patent is extended or adjusted under 35 U.S.C. 154(b) by 0 days.

(21) Appl. No.: 09/183,604

(22) Filed: Oct. 30, 1998

(65) Prior Publication Data

US 2003/0138968 A1 Jul. 24, 2003

(51) Int. Cl.[7] .................................................. B01L 1/00
(52) U.S. Cl. ........................ 422/100; 422/63; 422/81; 422/104; 436/180; 73/863.32; 73/864.72
(58) Field of Search ..................... 422/100, 63, 104, 422/81; 436/180, 174; 435/307.1, 287.2, 309.1, 309.3; 141/24, 25, 242, 234; 222/92, 94, 95, 263; 73/863.32, 864.72

(56) References Cited

U.S. PATENT DOCUMENTS

| 3,650,306 A | * | 3/1972 | Lancaster | ................... | 141/238 |
| 3,982,438 A | | 9/1976 | Byrd | ......................... | 73/425.6 |

(List continued on next page.)

FOREIGN PATENT DOCUMENTS

| DE | 4123660 C2 | 7/1993 | ............ C12N/11/12 |
| DE | 4217868 C2 | 1/1995 | ............ G01N/21/03 |
| DE | 4209064 C2 | 7/1995 | ............ B01L/11/00 |
| EP | 0110610 A2 | 6/1984 | ............. B01L/3/02 |
| EP | 0151005 A2 | 8/1985 | ............. B01L/3/02 |
| EP | 0215536 A2 | 3/1987 | ............. B01L/3/02 |
| EP | 0266155 A2 | 5/1988 | ............. B01L/3/02 |
| EP | 0304765 A2 | 3/1989 | ............ B01L/11/00 |
| EP | 0505004 A2 | 9/1992 | ............ G01N/35/06 |

(List continued on next page.)

OTHER PUBLICATIONS

Khrapko, K.R. et al., "A Method for DNA Sequencing by Hybridization with Oligonucleotide Matrix", *DNA Sequence—J. DNA Sequencing and Mapping*, vol. 1, pp. 375–388.

*Primary Examiner*—Jill Warden
*Assistant Examiner*—Kathryn Bex
(74) *Attorney, Agent, or Firm*—Gordon M. Stewart (57) ABSTRACT

Liquids are transferred from a plurality of wells or depots having openings arranged in a selected format to one or more receptacles, by displacing liquid contained in each well so that a convex meniscus swells from the opening, and contacting the receptacle with the swollen meniscus to draw a portion of the liquid into the receptacle. According to the invention, the liquid transfer is effected directly from the depot to the corresponding receptacle without contact between depots and receptacles, and without interposition of any transfer device between depots and receptacles. Apparatus for carrying out the method includes a depot member having a plurality of wells having openings supported in a selected format, and a receiving member defining at least one receptacle and usually a plurality of receptacles in a corresponding or complementary format; a device for displacing liquid contained within the wells toward and through the openings; and a device for bringing at least one selected well opening into proximity with at least one selected receptacle. In some embodiments the liquid is displaced by inwardly deforming portions of the walls of the wells; in other embodiments the liquid is displaced by introducing a displacing fluid into the wells at a point away from the openings. The inventions is particularly useful in transferring a multiplicities of liquids from preparative or storage depots to receptacles formed in planar members such as planar microfluidics devices or printing devices adapted for deposition of materials in microarrays.

6 Claims, 6 Drawing Sheets

U.S. PATENT DOCUMENTS

| | | | | |
|---|---|---|---|---|
| 4,047,438 A | * | 9/1977 | Sekine | 73/423 |
| 4,099,550 A | * | 7/1978 | Matsuzaki et al. | 141/51 |
| 4,158,035 A | * | 6/1979 | Haase et al. | 422/100 |
| 4,444,062 A | * | 4/1984 | Bennett et al. | 73/863.32 |
| 4,461,328 A | * | 7/1984 | Kenney | 141/67 |
| 4,511,534 A | * | 4/1985 | Bennett, Jr. et al. | 422/100 |
| 4,532,805 A | * | 8/1985 | Flesher | 73/863.32 |
| 4,537,231 A | * | 8/1985 | Hasskamp | 141/238 |
| 4,626,509 A | * | 12/1986 | Lyman | 435/287 |
| 4,788,557 A | * | 11/1988 | Howkins | 346/1.1 |
| 4,870,431 A | * | 9/1989 | Sousa et al. | 346/140 |
| 4,877,745 A | * | 10/1989 | Hayes et al. | 436/166 |
| 5,106,592 A | | 4/1992 | Stapelmann et al. | 422/245 |
| 5,110,406 A | | 5/1992 | Sill et al. | 156/621 |
| 5,204,268 A | | 4/1993 | Matsumoto | 436/44 |
| 5,254,313 A | | 10/1993 | Kuroda et al. | 422/100 |
| 5,256,573 A | | 10/1993 | Kuroda et al. | 436/179 |
| 5,338,688 A | * | 8/1994 | Deeg et al. | 436/180 |
| 5,343,909 A | * | 9/1994 | Goodman | 141/242 |
| 5,348,606 A | * | 9/1994 | Hanaway et al. | 156/292 |
| 5,445,797 A | * | 8/1995 | Flesher | 422/100 |
| 5,449,754 A | | 9/1995 | Nishioka | 530/334 |
| 5,474,796 A | | 12/1995 | Brennan | 427/2.13 |
| 5,601,980 A | | 2/1997 | Gordon et al. | 435/6 |
| 5,658,802 A | * | 8/1997 | Hayes et al. | 436/518 |
| 5,700,637 A | | 12/1997 | Southern | 435/6 |
| 5,756,050 A | | 5/1998 | Ershow et al. | 422/100 |
| 5,763,278 A | * | 6/1998 | Sickinger et al. | 436/180 |
| 5,914,732 A | * | 6/1999 | Sakai et al. | 347/10 |
| 5,980,719 A | | 11/1999 | Cherukuri et al. | |
| 6,082,185 A | * | 7/2000 | Saaski | 73/64.56 |
| 6,090,251 A | * | 7/2000 | Sundberg et al. | 204/453 |
| 6,103,199 A | | 8/2000 | Bjornson et al. | |
| 6,251,343 B1 | | 6/2001 | Dubrow et al. | |
| 6,284,113 B1 | * | 9/2001 | Bjornson et al. | 204/453 |
| 6,287,872 B1 | * | 9/2001 | Schuorenberg et al. | 436/181 |
| 6,296,702 B1 | * | 10/2001 | Bryning et al. | 118/401 |

FOREIGN PATENT DOCUMENTS

| | | | | |
|---|---|---|---|---|
| EP | 0608423 A1 | 8/1994 | | G01N/35/06 |
| EP | 0670483 A2 | 9/1995 | | G01N/1/38 |
| EP | 0820811 A2 | 1/1998 | | B01L/3/02 |
| WO | WO 95/35505 | 12/1995 | | G01N/33/543 |
| WO | WO97/15394 A1 | 5/1997 | | B01L/3/00 |
| WO | WO98/55852 A1 | 12/1998 | | G01N/27/26 |

* cited by examiner

METHOD AND APPARATUS FOR LIQUID TRANSFER

BACKGROUND

This invention relates to transferring liquids from one container to another, and more particularly the invention relates to methods and apparatus for transferring small quantities of liquids from a multiplicity of depots to a multiplicity of receptacles.

Continuing rapid advances in chemistry, particularly in biochemistry and molecular biology, demand improved capabilities for carrying out large numbers of reactions using small quantities of materials.

In screening patients for genetic disease and susceptibility, for example, the number of conditions for which associated mutations are known is growing, and the numbers of mutant alleles known to be associated with these conditions is increasing. An adequate genetic screen for one or even a few of these conditions can require testing a sample from the patient against a very large number of genetic probes.

Enormous and rapidly increasing numbers of critical biomolecules have been identified and characterized, and an understanding of their various roles in cellular processes is vastly improving. Consequently, for example, the number of potential targets for pharmacologic intervention is very large. Techniques for parallel chemical synthesis, such as combinatorial chemistries, can efficiently produce libraries of large numbers of synthetic compounds that may be screened against selected targets in a rational drug design approach.

Considerable effort has been directed to developing better approaches to handling large numbers of samples, reagents and analytes. Automated laboratory workstations and robotics-based systems have been brought to routine use for some chemical manipulations in screening and synthesis, and dedicated computer applications have been developed both for controlling processes and for manipulating data. And a number of approaches have been proposed for miniaturizing systems for carrying out chemical processes, to reduce the quantities of the various components. Some of these approaches have found use. Particularly, for example, array technologies for binding pair assays use components immobilized in arrays of features on a surface; and microfluidics technologies employ networks of interconnected capillaries to move and combine components on a very small scale.

There is significant and growing interest in employing array technologies for conducting biomolecular manipulations. In array techniques certain of the components are immobilized in a pattern of array features on a surface of a solid support, and permitted to interact with other components. Arrays of binding agents, in which such binding agents as oligonucleotides or peptides are deposited onto a support surface in the form of an array or pattern, can be useful in a variety of applications, including gene expression analysis, drug screening, nucleic acid sequencing, mutation analysis, and the like. For example, information about the nucleotide sequence of a target nucleic acid may be obtained by contacting the target with an array of different surface-bound DNA probes under conditions that favor hybridization of nucleic acids having complementary sequences, and determining at what sites on the array nucleic acid duplexes are formed. Hybridization to surface-bound DNA probe arrays can provide a relatively large amount of information in a single experiment. And, for example, array technology can be useful in differential gene expression analysis.

Such arrays may be prepared in any of a variety of different ways. For example, DNA arrays may be prepared manually by spotting DNA onto the surface of a substrate with a micro pipette. See, Khrapko et al. (1991), DNA Sequence 1:375–388. Or, a dot-blot approach or a slot-blot approach may be employed in which a vacuum manifold transfers aqueous DNA samples from a plurality of wells to a substrate surface. Or, an array of pins can be dipped into an array of fluid samples and then contacted with the substrate surface to produce the array of sample materials. Or, an array of capillaries can be used to produce biopolymeric arrays, as described for example in International Patent Publication WO 95/35505.

U.S. patent applications Ser. Nos. 09/150,504 and 09/150,507 describe forming biomolecular arrays by adaptations of devices employed in the printing industry and, particularly, of inkjet print heads and of automated devices for moving a print head over a print surface and for depositing the inks at desired locations on the surface. These references and others cited herein, above and below, are incorporated herein in their entirety by reference. Other uses of inkjet printing devices to dispense biochemical agents such as proteins and nucleic acids are suggested or disclosed in, for example, U.S. Pat. Nos. 5,658,802; 5,338,688; 5,700,637; 5,474,796; 4,877,745; and 5,449,754.

Whether the miniaturized system is a microfluidic device or an array, or is of some other design, at least some of the various biomolecules to be introduced to the system are typically prepared in depots remote from the receptacles by which they are introduced to the system. These depots may take the form of a multiwell plate (conventionally providing 96 wells in a 12×8 format), for example, or a microtiter plate (conventionally providing 384 wells in a 16×24 format, or 1536 wells in a 32×48 format). A technical challenge is presented by the step of transferring the liquids containing the various biomolecules from the depots to the specific receptacles. In an array system constructed using an inkjet printing technique, for example, a technical challenge is presented by the need to transfer the liquids from the depots to the specific reservoirs in the print head.

Conventionally a pipet may be employed to transfer a liquid dropwise from a depot to a receptacle (such as a reservoir in a microfluidics device or a reservoir in a print head). The tip of the pipet is first dipped into the liquid in the depot and some of the liquid is drawn into the pipet; then the pipet is moved to the receptacle and a quantity of the liquid is expelled into the receptacle. Several pipets may be ganged and used to transfer several different liquids at once, to reduce the number of repetitions, but problems of small dimension may make such an approach impractical. In any event the transfer step results in contamination of pipets, which accordingly must be either discarded and replaced or decontaminated (for example by rinsing) before they are used to transfer different liquids. Where a large number of different liquids are to be moved, the transfer apparatus becomes mechanically unwieldy, and the cost of minimizing the risk of contamination is increased.

SUMMARY OF THE INVENTION

In one general aspect the invention features a method for transferring liquids from a plurality of wells to one or more receptacles, by displacing liquid contained in each well so that a convex meniscus swells from the opening of the well, and contacting a receptacle with the swollen meniscus to draw at least a portion of the liquid into the receptacle. According to the invention, the liquid transfer is effected directly from the depots to the corresponding receptacles without contact between depots and the receptacles, and without interposition of any transfer device between depots and the receptacles. And, according to the invention, the flow of the liquid into the receptacle following contact of the receptacle with the meniscus is at least initially a result of capillary interaction, and ordinarily is principally so.

In preferred embodiments the wells are arranged in a specified pattern in a depot member, so that where different wells contain different liquids or contain liquids containing different constituents, the different liquid contents are associable with the positions of the wells in the pattern. And, in some embodiments where liquids from different wells are to be transferred to specified different receptacles, the receptacles are arranged in a corresponding or complementary pattern, so that a specified plurality of the wells may be aligned with a corresponding specified plurality of the receptacles, so that transfer of the liquids may be accomplished all at once from the specified wells to the specified receptacles.

Accordingly in another aspect the invention features a method for transferring liquids from a plurality of wells having openings arranged in a selected format to a plurality of receptacles arranged in a corresponding or complementary format, by displacing the liquid contained in each well so that a convex meniscus swells from the opening, and contacting the corresponding receptacle with the swollen meniscus to draw a portion of the liquid into the receptacles.

In some embodiments the liquid displacing step is carried out by inwardly deforming a wall of each well to displace the liquid; in preferred embodiments the wall is inwardly deformed by application of mechanical or fluid pressure to the wall. In other embodiments the liquid displacing step is carried out by introducing a gas into a part of each well away from the opening; in preferred embodiments the gas is introduced through a vent in a part of the wall away from the opening, and in some embodiments the gas is passed through a gas-permeable membrane covering the vent.

In some embodiments the arrangements of the well openings and the receptacles is such that receptacles to which transfer of liquid is specified may come into contact with swollen menisci at the openings of specified wells. In some embodiments the arrangement of either the well openings or the receptacles is in a generally planar format, and the step of contacting the receptacles with the menisci is carried out by bringing the specified receptacles with the menisci at the specified well openings. Or, the arrangement of the well openings and the arrangement of receptacles each is in a generally planar format, and the step of contacting the receptacles with the menisci is carried out by bringing the well openings into respective planes into generally parallel proximity.

In another general aspect the invention features apparatus for transferring a plurality of liquids, the apparatus including a depot member having a plurality of wells each having an inwardly deformable wall portion and an opening, in which the openings are supported in a selected format, and a member defining a plurality of receptacles in a corresponding or complementary format; means for displacing liquid contained within the wells toward and through the openings; and means for bringing well openings and receptacles into proximity. According to the invention, transfer of liquid is effected by deploying the displacing means to displace the liquid in the well, causing a convex meniscus to swell outward from the opening. When a receptacle which has been brought into proximity contacts the swollen meniscus, the liquid is drawn into the receptacle. The apparatus for effecting the transfer is uncomplicated and can be made in a straightforward manner from inexpensive materials using simple tools.

It can for some processes be advantageous to transfer a multiplicity of liquids from a multiplicity of specified wells or depots to a multiplicity of assigned or specified receptacles in a single transfer operation. Accordingly in some embodiments the well openings and the receptacles are arranged so that a multiplicity of corresponding or complementary receptacles and wall openings can be brought into proximity simultaneously, so that the receptacles contact the respective menisci at nearly the same time. Where the well openings are arranged in a generally planar pattern, for example, liquid droplets expressed at a line of such wells may in one step be transferred into a line of receptacles that are brought into generally parallel proximity with the line of wall openings; or, liquid droplets at a planar group of such wells may in one step be transferred into a complementary group of receptacles, themselves arranged in a generally planar pattern, that are brought into generally parallel proximity with the group of well openings.

Accordingly, in some embodiments the receptacle-defining member is generally planar, and the well openings are supported in a generally planar format. In some embodiments the receptacle-defining member is an orifice plate of a print head and the receptacles are in fluid communication with reservoirs in the print head; and in some embodiments the print orifices are the receptacles.

In some embodiments the wells include a deformable wall portion, and the means for displacing the liquid in the wells include means for inwardly deforming the deformable wall portion. In some embodiments the wall-deforming means includes mechanical means such as a plunger for pressing against an outer surface of the deformable wall portion; or means for applying fluid pressure (liquid or gas) at the outer surface of the deformable wall portion.

In other embodiments each well includes a vent positioned away from the opening, and means for introducing a fluid (gas or liquid) through the vent and into the well, to displace the liquid in the well toward the opening. In preferred embodiments the vent is covered by a membrane that retains the liquid in the well under operating conditions, but is permeable to the fluid to be introduced through the vent into the well to displace the liquid in the well.

In some embodiments the well includes a rigid wall portion in addition to the deformable wall portion, and in some embodiments the inwardly deformable wall portion and the rigid wall portion are formed of a unitary piece of material. In some embodiments the inwardly deformable wall portion includes a plastic or elastic film. In some embodiments the inwardly deformable wall portion and the support for the well openings are formed of a unitary piece of material.

Other aspects and advantages of the invention will become apparent from the following detailed description, taken together with the accompanying drawings, illustrating by way of example the principles of the invention.

DRAWINGS

The drawings are for purposes of illustration, and the figures are presented in diagrammatic form and are not made to scale.

DETAILED DESCRIPTION

As the drawings show by way of illustration, the invention is embodied in apparatus for direct non-contact transfer of fluids from a plurality of depots, or wells, having openings arranged in a specified pattern, to a plurality of receptacles arranged in a corresponding or complementary pattern. In particular embodiments the liquid contained in the wells is displaced so that a convex meniscus swells outward from the openings, and the liquid flows into the receptacles upon contact of the receptacle with the convex meniscus. The flow of the liquid into the receptacle following contact of the receptacle with the meniscus is at least initially a result of capillary interaction.

Figure 1A:
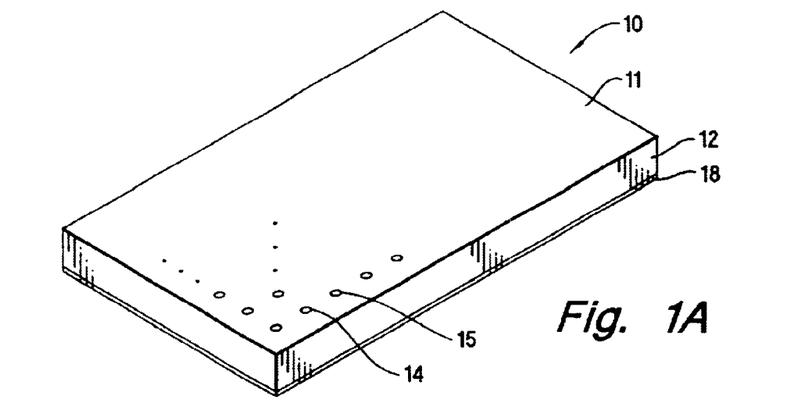
FIG. 1A is a sketch of an embodiment of the invention in a perspective view.

Referring now to FIG. 1A, there is shown in a perspective view an embodiment generally at 10 of a block 12 of depots 14, from which liquids are to be transferred according to the invention to reservoirs arranged in a corresponding pattern. In this illustrative embodiment, as appears also in FIG. 1B, the depots 14 are arranged as wells of a standard 16×24 microtiter plate (not all the wells are drawn in the Fig.). As may be understood more clearly by reference to FIG. 1C, depot block 12 has a generally planar surfaces 11 and 13, and each generally cylindrical depot 14 is defined by a generally cylindrical rigid wall 16 passing from surface 11 through to surface 13 of depot block 12 and having a generally circular opening 15 at surface 11 and a generally circular opening 17 at surface 13. Depot block surface 13 is covered with a plastic or elastic film 18, which is sealed to surface 13 at least at the margins of circular openings 17. Accordingly, the circular depot openings 15 are arranged in a generally planar pattern, and the portions of the elastic film 18 that cover the circular openings 17 form the deformable wall portions 19 of the depots.

Figure 1B:
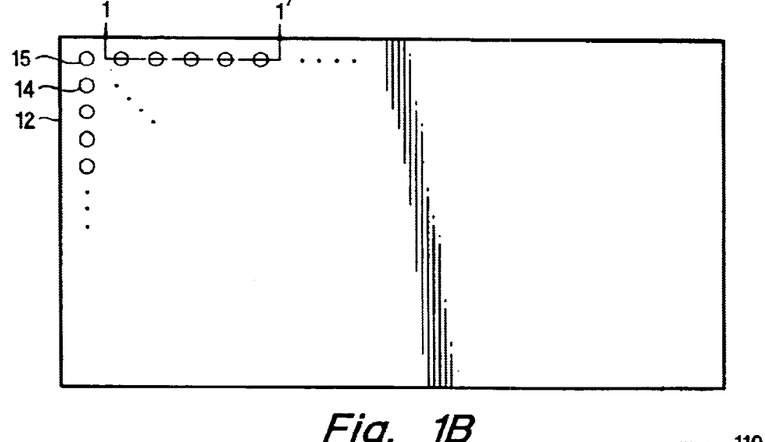
FIG. 1B is a sketch in a plan view of the embodiment of FIG. 1A.
Figure 1C:
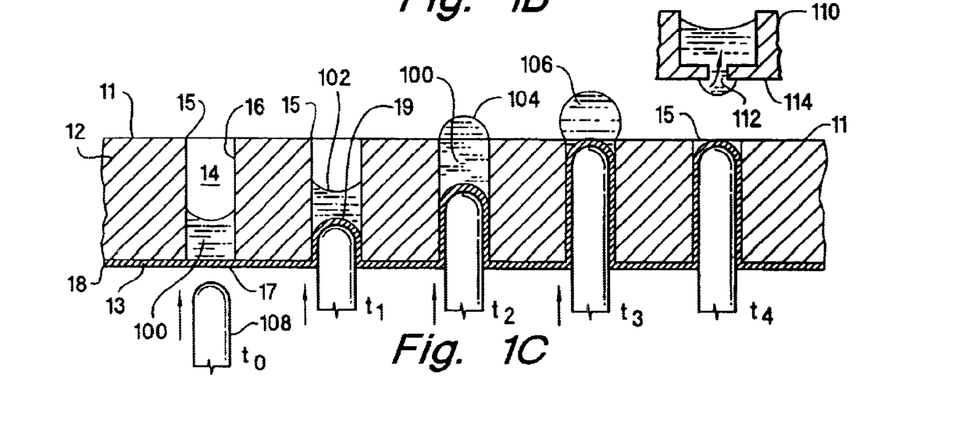
FIG. 1C is a sketch in sectional view thru 1–1' of the embodiment of FIG. 1B, showing in wells from left to right the progress of forming a convex meniscus at the well opening by inward displacement of a portion of the wall, and showing at right the transfer of the liquid to a receptacle brought into contact with the convex meniscus.

The embodiment of FIGS. 1A–1C can be employed in the method of the invention as follows. Referring to FIG. 1C, which is a composite showing a time course ($t_0$ through $t_4$) from left to right, a quantity of liquid 100 is held in each depot. In practice, the liquid in each depot may have a specified character, or the liquid in each depot may contain a specified biomolecule or reagent or analyte, or a specified mixture of biomolecules or reagents or analytes. The liquids may simply be stored in the depots, or they may have been prepared in the depots at least in part. The depots may be entirely filled with the liquids or, as illustrated in FIG. 1C ($t_0$), they may be only partly full. Transfer from a depot is initiated ($t_1$) by applying a force against the deformable wall portion 19, deforming it inward and displacing the liquid 100 within the depot. The wall may be deformed by any of a variety of means for applying force; one such means, shown by way of illustration in FIG. 1C, is to press a plunger 108 inwardly against the outer surface of the deformable wall portion. The progressively increasing inward deformation of the wall causes the meniscus 102 of the liquid to rise toward ($t_1$) and through ($t_2$) the opening 15, forming a convex meniscus 104. As the liquid 100 is further displaced ($t_3$) the convex meniscus 104 rises and swells as a droplet 106 of the liquid is held by surface interaction away from the opening 15 and the depot block surface 11. The transfer is completed ($t_4$) by contacting the swollen convex meniscus 104 with a receptacle 110, which may for example be an orifice 112 in a planar receiving member 114. Surface interaction of the receptacle 110 with the liquid results in movement of the droplet of fluid 106 away from the depot block surface 11 and the opening 15 and into the receptacle 110.

As will be appreciated, a multiplicity of particular liquids (or constituents in liquid carriers) can according to the invention be rapidly and reliably transferred directly to assigned receptacles (for example, to assigned reservoirs in a printing device for constructing a biomolecular array; or to particular reservoirs in a microfluidic device). The particular liquids are held in particular depots whose positions in the depot block correspond to the respective positions of the assigned receptacles in the receiving member; the contents of the depots are displaced to form droplets at the openings of the particular depots; and, where transfer of a plurality of liquids at once is desired, the receiving member is brought into parallel proximity to the depot block surface so that the receptacles contact the menisci of the respective droplets at nearly the same time.

As will be appreciated, a receptacle is in proximity to a well or depot opening when it is close enough to make contact with the swollen meniscus of a droplet at the opening. Where a meniscus swells to a greater distance from the opening, proximity is reached at a greater distance between the receptacle and the opening. In practice there may be some variation in the distances to which the various menisci swell away from the openings and, where a plurality of droplets are to be transferred in a single transfer step, some of the droplets may pass into their respective receptacles at greater distances than other. Or, if the receptacles and the openings are first brought to a given narrow separation, within the range of distances to which the menisci may be expected to swell, and then the displacement of the liquids progresses, some of the droplets may contact the receptacles earlier than others. In either event, a transfer step constitutes moving the receptacles and openings together until the desired transfers of swollen droplets have been effected, or holding the receptacles and openings at a given narrow separation and then progressively swelling the droplets of the liquids whose transfer is desired until all the menisci have traversed the separation, contacted the receptacles, and been drawn into the receptacles. As will be appreciated, the distance to which a droplet may swell away from the opening depends upon a variety of factors, including among others characteristics of the liquid, characteristics of the surfaces at the openings, shapes and dimensions of the openings, and the like. According to the invention, the receptacle makes no contact with the opening during the transfer.

Figure 7:
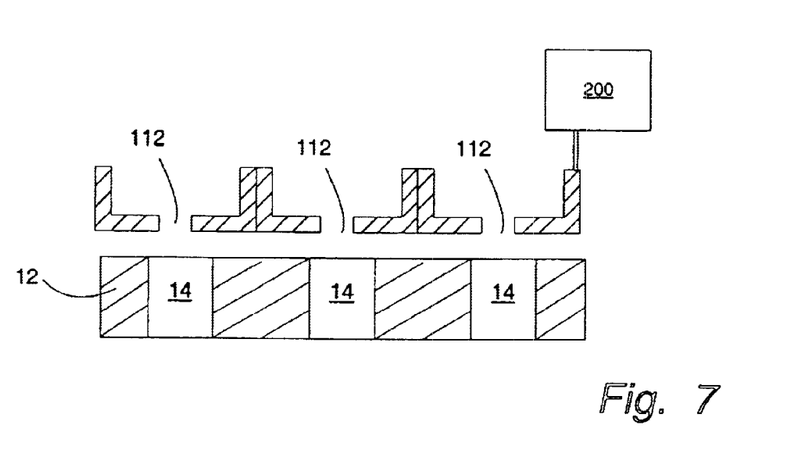
FIG. 7 shows a member with a plurality of receptacles

Any of a variety of means can be employed for bringing receptacles into contact with menisci according to the invention, any of which will be within the knowledge of the person of ordinary skill. They may be brought into proximity together by hand, for example, by holding either the member supporting the wells or the member supporting the receptacles, or both of them, in hand. As will be appreciated, however, a straightforward mechanical method may be preferred, to ensure precision and to complete the transfer step more rapidly. Where the transfer is from a multiwell plate to a printhead, for example, the mechanism 200 (see FIG. 7) that positions and moves the printhead over the printed surface can also be employed to bring the printhead and the multiwell plate into proximity.

A prototype of the embodiment shown in FIGS. 1A–1C was conveniently constructed by modification of a conventional polystyrene microtiter plate, commercially available under the name Greiner, generally as follows. First, the lower part of the microtiter plate was cut away to remove the bottom parts of the wells and to provide a depot block about 25 mm long and 25 mm wide and 4 mm thick, having roughly square bores arranged in the 11×11 orthogonal pattern of the microtiter wells. The depots were about 1.5 mm on each side and orthogonally adjacent depots were spaced apart at 2.25 mm center-to-center. Then an elastomeric film, of latex having 6 mil thickness, was affixed to the cut surface of the depot block, and sealed using an epoxy, to provide the deformable wall portions of the depots.

The prototype constructed in this fashion and having these dimensions and operated generally as described above with reference to FIG. 1C, using water as a liquid for purposes of demonstration, proved capable of raising a convex meniscus to a height of about 1 mm away from the opening at the surface of the depot block. For purposes of demonstration the orifice plate of a print head was brought into generally parallel proximity to the surface of the depot block, with the print head orifices approximately aligned with the centers of the depots. As the orifice plate was moved close enough to the depot block, the print head orifice contacted the convex meniscus, and substantially all the liquid that had been displaced through the opening was transferred into the print head through the print head orifice.

The size of each orifice in the orifice plate is one that produces a spot of suitable dimensions on the substrate surface, where the orifice generally has an exit diameter (or exit diagonal depending upon the particular format of the device) in the range about 1 $\mu$m to 1 mm, usually about 5 $\mu$m to 100 $\mu$m, and more usually about 10 $\mu$m to 60 $\mu$m. A means may be associated with each orifice for propelling fluid through the associated orifice from a delivery chamber that is in fluid conducting relationship with the orifice. In some embodiments the propelling means propels the fluid through the associated orifice by forming a bubble that displaces the fluid; particular bubble-forming means include a source of heat such as an electrical resistor. In other embodiments the propelling means propels the fluid through the associated orifice by electromechanical displacement; particular electromechanical displacement means include a piezoelectric device.

As may be appreciated by one of skill in the art, and as will be discussed in further detail below, other methods of fabrication and other starting materials are contemplated, and other dimensions and configurations for the depot block and the depots and their various parts are within the scope of the invention.

In the prototype described above an elastomeric material constituted the deformable wall portion. In this construction, once a transfer has been completed and the deforming force is removed (for example, by withdrawing the plunger), the wall returns elastically to approximately its original shape. This permits re-use of the device, which may be desired for example where aliquots of the liquid are to be transferred at time intervals or following a sequence of treatment steps in the depot. Alternatively, a plastic material may be used for the deformable wall portion and, in this construction, the deformed wall does not return to its original shape.

Figure 2A:
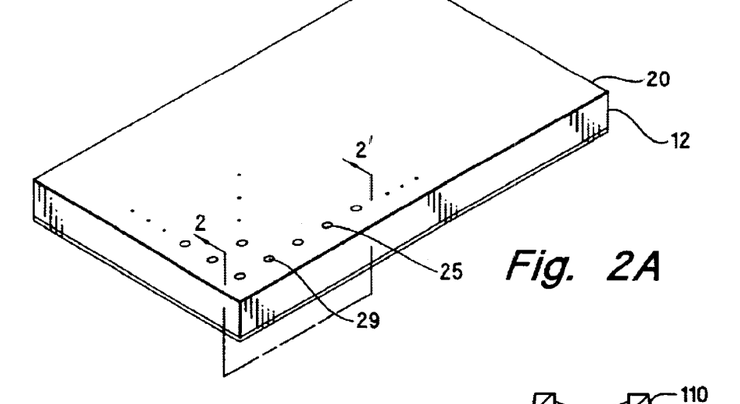
FIG. 2A is a sketch of an alternative embodiment of the invention in a perspective view.
Figure 2B:
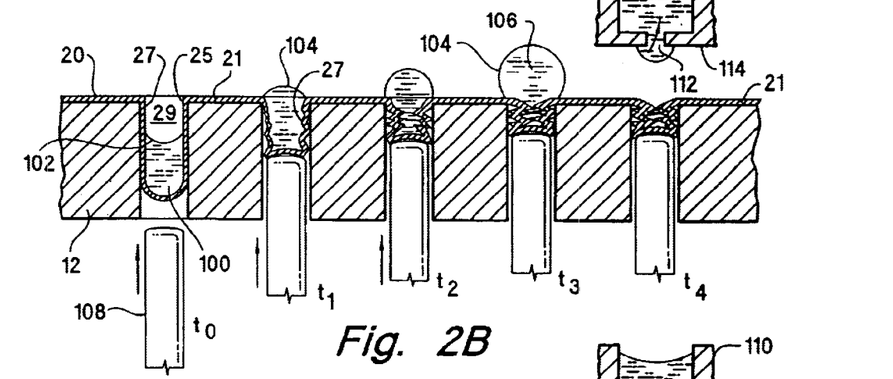
FIG. 2B is a sketch in sectional view thru 2–2' of the embodiment of FIG. 2A, showing in wells from left to right the progress of forming a convex meniscus at the well opening by inward displacement of a portion of the wall by buckling or collapsing the wall portion, and showing at right the transfer of the liquid to a receptacle brought into contact with the convex meniscus.
Figure 3:
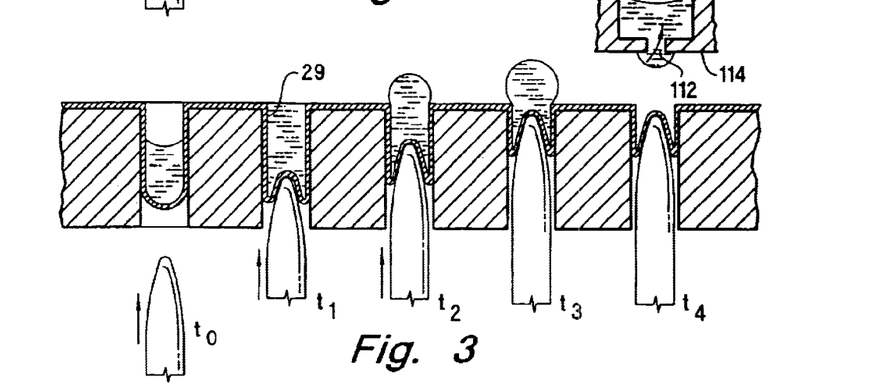
FIG. 3 is a sketch in sectional view as thru 2–2' of an embodiment as in FIG. 2A, showing in wells from left to right the progress of forming a convex meniscus at the well opening by inward displacement of a portion of the wall by partially turning the wall portion inside out, and showing at right the transfer of the liquid to a receptacle brought into contact with the convex meniscus.

A variety of different configurations are made possible by employing a nonelastomeric material for the deformable wall portion. Illustrative examples are shown in FIGS. 2A and 2B; FIGS. 3A and 3B; and FIGS. 4A and 4B. Each of these illustrative embodiments is a laminate structure that includes as one lamina a plastic film that has been shaped to provide the desired deformable walls.

Figure 5A:
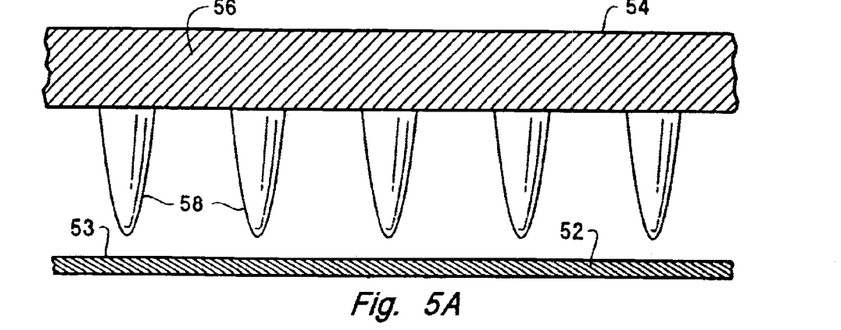
FIGS. 5A–C are sketches in sectional view as for example in FIG. 2B, showing stages in fabrication of the deformable wall portions by pressing an array of mandrels against a plastic film.
Figure 5B:
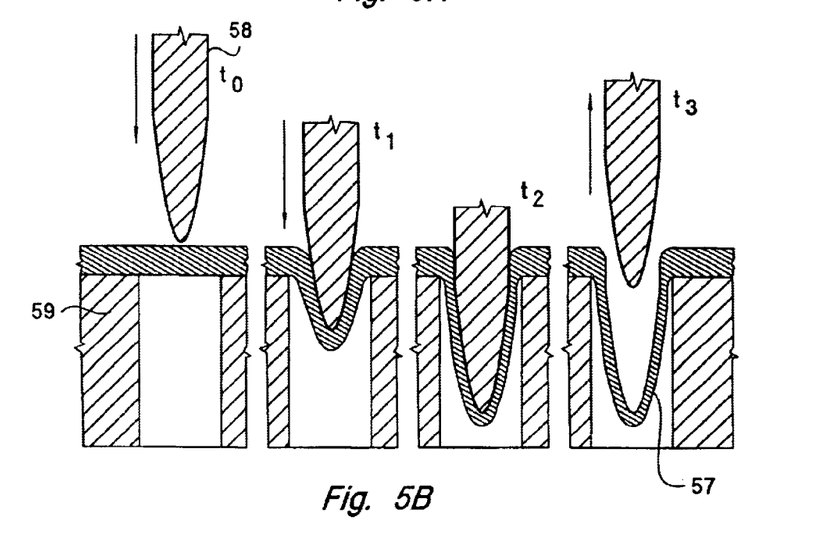
Figure 5C:
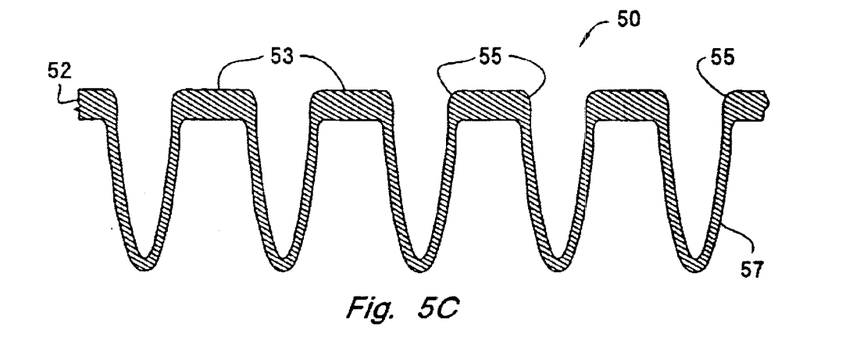

A preferred cold-forming method for shaping the film is described by reference to FIGS. 5A–5C. Referring to FIG. 5A, the starting material is a piece of plastic film 52, which is dimensioned to accommodate the desired pattern of depots. A press 54 is provided, consisting of mandrels 58 projecting from a block member 56. The press 54 is then moved against a surface 53 of the film 52, such that the mandrels 58 press into and shape the film, as shown in progress in a time sequence ($t_0$ through $t_3$) for a single depot in sectional view in FIG. 5B. A die 59 may be provided to support the film during the cold-forming process. The shaping is continued until the desired shape 50 is complete, as shown in sectional view in FIG. 5C. The press is then removed from the film, causing the mandrels to withdraw from the now-shaped depot walls 57, as shown in sectional view in FIG. 5C. The shapes and dimensions of the mandrels 58 are made to provide the desired shapes for the depots they form; and the positions of the mandrels 58 on the block member 56 correspond to the desired pattern of the wells. An illustrative example of a completed cold-formed structure appears in FIG. 5C, showing deformable depot walls 57 having-openings 55 onto what remains of the surface 53 of the starting film 52. The deformable walls 57 are by virtue of attenuation during the cold forming process made thinner than the original film 52. The desired thickness of the deformable walls 57 can be determined as a matter of design routine; it depends principally upon the characteristics of the particular plastic material used, the dimensions of the deformable wall portion, and the design and construction of the means for deforming the wall. As will be appreciated, the unattenuated portion of the original film that remains among the openings 55 of the deformable walls 57 supports the desired structure 50, and it may be sufficiently rigid to serve as a depot block in the course of the transfer process. More usually, however, further support will be required, as in the exemplary embodiments described below.

Referring now to FIGS. 2A and 2B, there is shown an embodiment in which a shaped film 20, cold-formed as described above with reference to FIGS. 5A–5E to make openings 55 and deformable depot walls 57, which depend from what remains among the openings of the original film 52. In this embodiment the shaped film 20 is supported by a block 12, which conveniently may have served as a die 59 during the cold-forming process. The deformable walls 57 constitute the depots 29, and the generally circular openings 55 form the openings 25 at the surface 21 at which the droplets are formed during the transfer process. That is, the liquid in the depots is confined within and is transferred from the deformable depot walls in this embodiment.

The embodiment of FIGS. 2A and 2B can be employed in the method of the invention as follows. Referring to FIG. 2B, which generally as in FIG. 1C is a composite showing a time course ($t_0$ through $t_4$) from left to right, a quantity of liquid 100 is held in each depot. As described above with reference to FIG. 1C, the depots may be entirely filled with the liquids or, as illustrated in FIG. 2B ($t_0$), they may be only partly full. Transfer from a depot is initiated ($t_1$) by applying a force against the deformable wall portion 29, deforming it inward and displacing the liquid 100 within the depot. The wall may be deformed by any of a variety of means for applying force; one such means, shown by way of illustration in FIG. 2B, is to press a plunger 108 inwardly against the outer surface of the deformable wall portion. This results in a progressive collapse ($t_1$ through $t_3$) of the deformable wall portion 29, which causes the meniscus 102 of the liquid to rise toward ($t_1$) and through ($t_2$) the opening 25, forming a convex meniscus 104. As the liquid 100 is further displaced ($t_3$) the convex meniscus 104 rises and swells as a droplet 106 of the liquid is held by surface interaction away from the opening 25 and the depot block surface 21. The transfer is completed ($t_4$) by contacting the swollen convex meniscus 104 with a receptacle 110, which may for example be an orifice 112 in a planar receiving member 114. Surface interaction of the receptacle 110 with the liquid results in movement of the droplet of fluid 106 away from the depot block surface 21 and the opening 25 and into the receptacle 110.

FIG. 3 shows a liquid transfer process employing an embodiment constructed generally as in FIG. 2B, except this process employs a plunger 118 shaped to turn the deformable wall portion 29 partially inside out, rather than collapse it. This manner of deformation may be preferred for some deformable wall materials and deformable wall thicknesses, to provide adequate displacement of liquid without rupture of the wall.

Figure 4A:
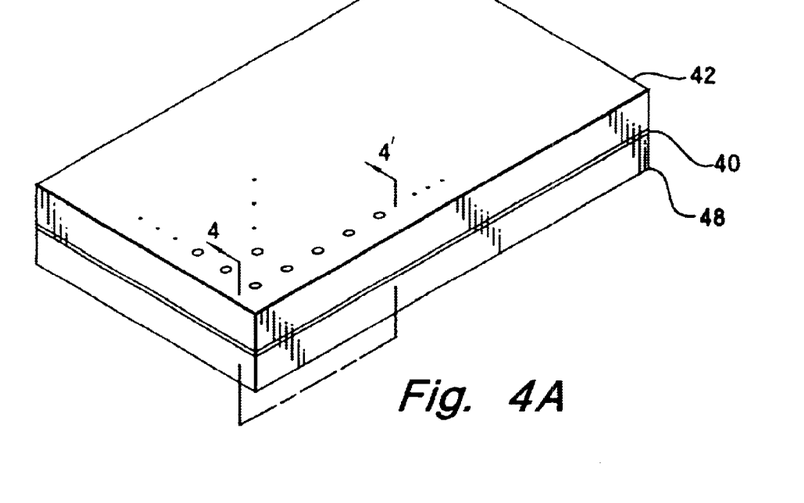
FIG. 4A is a sketch of a further embodiment of the invention in a perspective view.
Figure 4B:
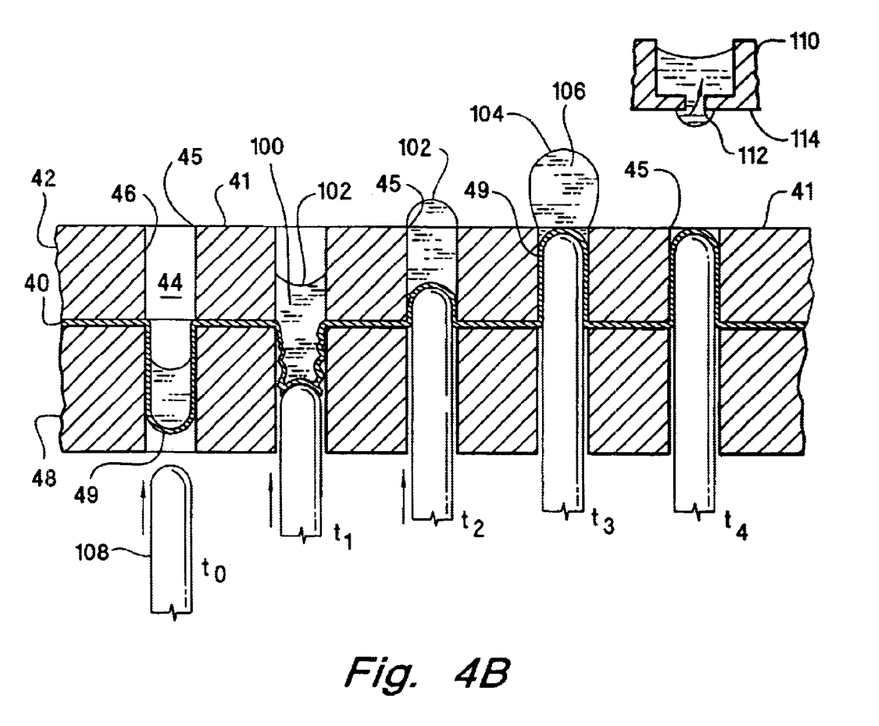
FIG. 4B is a sketch in sectional view thru 4–4' of the embodiment of FIG. 4A, showing in wells from left to right the progress of forming a convex meniscus at the well opening by inward displacement of a portion of the wall by inverting the wall portion, and showing at right the transfer of the liquid to a receptacle brought into contact with the convex meniscus.

FIGS. 4A, 4B show yet another embodiment, which may be viewed as a structural hybrid of the embodiments of FIGS. 1A and 2C. In this embodiment a shaped film 40 is interposed between an exit block 42 and a support block 48. Exit block 42 is provided with generally cylindrical bores having cylindrical rigid walls 46, opening by way of generally circular openings 45 at surface 41. As is described generally with reference to FIGS. 2A and 2B, shaped film 40 is cold-formed to make deformable wall portions 49, which depend into generally cylindrical bores in support block 48, which may conveniently have served as a die 59 during the cold-forming process. As will appear from inspection of FIG. 4B, the fluid capacity of the depots 44 in this embodiment includes both the cylindrical volume enclosed within the rigid cylindrical walls 46 and the volume enclosed by the depending deformable wall portions 49.

As shown in a composite showing a time course from left to right, generally as shown in FIG. 2A, transfer from a depot 44 is initiated ($t_1$) by applying a force against the deformable wall portion 49, deforming it inward and displacing the liquid 100 within the depot. The wall may be deformed by any of a variety of means for applying force; one such means, shown by way of illustration in FIG. 4B, is to press a plunger 108 inwardly against the outer surface of the deformable wall portion. This results in progressively collapsing the deformable wall portion 49 and then turning it inside out ($t_1$ through $t_3$). This causes the meniscus 102 of the liquid to rise toward ($t_1$) and through ($t_2$) the opening 45, forming a convex meniscus 104. As the liquid 100 is further displaced ($t_3$) the convex meniscus 104 rises and swells as a droplet 106 of the liquid is held by surface interaction away from the opening 45 and the depot block surface 41. The transfer is completed ($t_4$) by contacting the swollen convex meniscus 104 with a receptacle 110, which may for example be an orifice 112 in a planar receiving member 114. Surface interaction of the receptacle 110 with the liquid results in movement of the droplet of fluid 106 away from the depot block surface 41 and the opening 45 and into the receptacle 110.

Figure 6A:
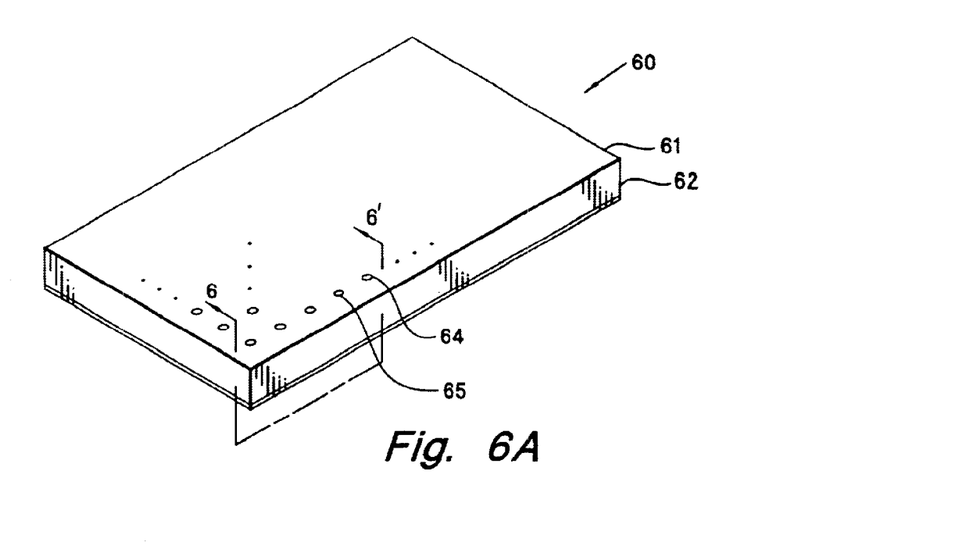
FIG. 6A is a sketch of a further embodiment of the invention in a perspective view.
Figure 6B:
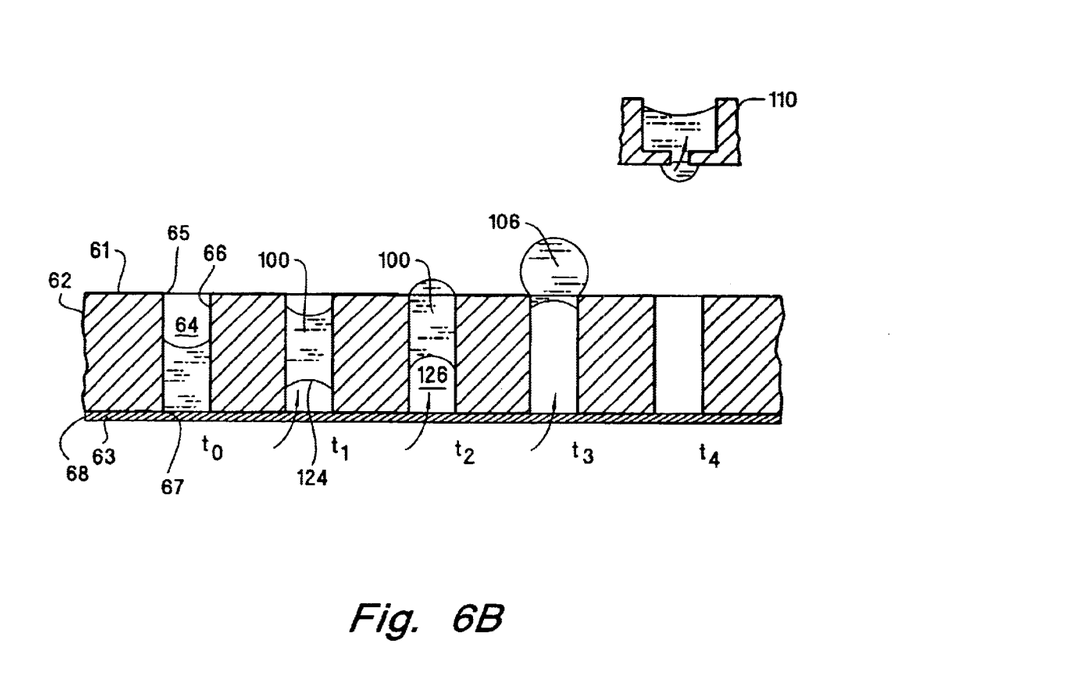
FIG. 6B is a sketch in sectional view thru 6–6' of the embodiment of FIG. 6A, showing in wells from left to right the progress of forming a convex meniscus at the well opening by introducing a gas through a gas-permeable membrane covering a vent in the wall, and showing at right the transfer of the liquid to a receptacle brought into contact with the convex meniscus.

FIGS. 6A, 6B show an alternative embodiment of the invention, in which displacement of the liquid in the depot is accomplished by introducing a gas into the depot by way of a vent, forming a bubble. The structure, shown generally at 60, is similar to that illustrated in FIGS. 1A–1C, except that a gas-permeable membrane is provided in place of the deformable elastomeric film. Referring now to FIGS. 6A and 6B, a block 62 contains generally cylindrical depots 64, each defined by a generally cylindrical rigid wall 66 passing from surface 61 through surface 63, and opening by way of generally circular openings 65 and 67 in surfaces 61 and 63, respectively. Depot block surface 63 is covered by a gas-permeable membrane 68, which is sealed to the surface 63 at least at the margins of circular openings 67. Gas-permeable membrane 68 inhibits escape of the liquid out from the depot, but permits passage of a gas into the depots by way of circular openings 67, which accordingly serve as vents.

As appears in a time course composite ($t_0$ through $t_4$) in FIG. 6B, the liquid in depot 64 is displaced by introducing the gas under pressure by way of the vents 67 through the membrane 68 to form ($t_1$) a second meniscus 124, concave with respect to the liquid, which, as a gas bubble 126 forms ($t_2$), advances away from the vent 67, displacing the liquid 100 away from the vent and toward the opening 65. As the liquid is further displaced ($t_3$) the convex meniscus 104 rises and swells as a droplet 106, which is then transferred ($t_4$) upon contact with the receptacle 110.

Suitable membrane materials may be selected by resort to materials specifications for commercially available membranes, for example, and tested using any desired displacement fluid without undue experimentation. Alternatively, the openings 67 may be covered by an impermeable material which is perforated to admit passage of the displacement fluid but not of the liquid to be transferred from the depot. Any fluid (liquid or gas) can be employed to displace the liquid 100, and the displacement fluid need not necessarily form a second meniscus 124. However, where it is desirable to minimize mixture of the displacement fluid with the liquid to be transferred from the depot, a relatively insoluble gas or immiscible liquid may be preferred.

The invention proves particularly useful for transfer of different liquids from a multiplicity of depots having openings arranged in a generally planar format to a multiplicity of receptacles, which may be correspondingly arranged in a generally planar format. The invention may be particularly useful for transferring liquids from arrays of preparative wells or storage depots, such as microtiter plates and the like, to receptacles on a surface of a microfluidics device or to apertures on the orifice surface of printing device employed in array deposition.

For transfer of liquids to a print head, U.S. patent applications Ser. Nos. 09/150,504 and 09/150,507 disclose loading the reservoirs of a printhead by way of the print orifices or other orifices in the orifice plate. For loading of nucleic acid compositions, for example, the orifice plate is contacted with the nucleic acid composition under conditions sufficient for fluid to flow through the orifice and into the firing chamber and reservoir of the head, where fluid flow is due, at least in part, to capillary forces. The invention provides for clean and straightforward presentation of a multiplicity of liquids such as nucleic acid compositions or other biomolecular preparations for contact with selected orifices in the orifice plate.

Other embodiments are within the following claims. For example, the depots may be arranged in other formats, standard to biochemistry and molecular biology or not. For transfer of a multiplicity of liquids in a single transfer step, all that is required of the format is that the depot openings and the receptacle openings be arranged in a format that permits bringing a multiplicity of receptacles into contact with the multiplicity of swollen menisci nearly all at once. That is, the respective receptacles and depot openings need only be arranged such that they can be brought into generally parallel proximity in a single transfer step.

For example, either the depot openings or the receptacles can be arranged on or in a generally planar support, and the other can be arranged generally on or in a cylindrical support; and the cylindrical support can be rotated about an axis parallel to the planar support and translated over it as if it were rolling upon an imaginary plane sufficiently close to the planar support that the receptacles contact swollen menisci at the depot openings and draw up the droplets as the movement progresses. Or, the depot openings and the receptacles each can be arranged on or in a generally cylindrical support, and the cylinders can be rolled to bring succeeding receptacles into contact with succeeding menisci. Other configurations will be apparent, and are within the scope of the invention.

And, for example, while the embodiments described herein by way of illustration generally have a laminate construction, in which for example the deformable depot walls are constructed from a film which is then affixed to a supporting member, it will be appreciated that any of the described embodiments may be constructed by forming the deformable walls and the supporting member or the deformable walls and the orifice block as unitary piece using techniques known in the plastics art. Such techniques include, for example, injection molding. The desired mechanical characteristics of the resulting parts may without undue experimentation be obtained by selection of suitable starting materials and configuration and dimensions.

And, for example, where the dimensions of a reservoir connected to the receptacle are small, or where channels leading from a receptacle to a reservoir are of small dimension or follow a long or tortuous path, loading of the channels or of the reservoir may be facilitated by applying a reduced pressure within the channel or reservoir to assist movement of the liquid through the receptacle. The transfer is preferably initiated, however, by capillary forces acting upon contact of the swollen meniscus with the receptacle.

We claim:

1. Apparatus for transferring a plurality of liquids, comprising a depot member having a plurality of wells each having an opening; a receiving member supporting a plurality of receptacles each having an orifice; means for displacing liquid contained within the wells toward and through the openings; and means for moving the well openings and receptacles into proximity such that liquid displaced through the wells openings contacts the receptacles at the orifice;

wherein the moving means moves the plurality of well openings and the plurality of the receptacles into proximity;

and wherein the receiving member comprises a print head carrying the plurality of receptacles that have the orifices through which fluid is propelled during printing.

2. The apparatus of claim 1 wherein the print head comprises means associated with each orifice for propelling fluid through the associated orifice.

3. The apparatus of claim 2 wherein the propelling means comprises a source of heat.

4. The apparatus of claim 2 wherein the propelling means comprises a piezoelectric device.

5. The apparatus of claim 1 wherein the print head comprises an orifice plate having the orifices therethrough.

6. The apparatus of claim 5 wherein the print head additionally includes reservoirs in the print head which are in fluid communication with the receptacles.

* * * * *